United States Patent [19]
Gerling et al.

[11] Patent Number: 5,525,333
[45] Date of Patent: Jun. 11, 1996

[54] LACTOBIONIC ACID AMIDE COMPOSITIONS AND THEIR USE

[75] Inventors: Klaus-Guenter Gerling, Laatzen; Sabine Joisten, Langenhaben; Kornelia Wendler, Sehnde; Claudia Schreer, Schellerten, all of Germany

[73] Assignee: Solvay Deutschland GmbH, Hanover, Germany

[21] Appl. No.: 359,181

[22] Filed: Dec. 19, 1994

Related U.S. Application Data

[62] Division of Ser. No. 136,371, Oct. 15, 1993, Pat. No. 5,401,426, which is a continuation of Ser. No. 974,164, May 11, 1992, abandoned.

[30] Foreign Application Priority Data

May 11, 1992 [DE] Germany .................. 42 15 478.2
May 7, 1993 [EP] European Pat. Off. ............. 93107417

[51] Int. Cl.⁶ .................. A61K 31/74; A61K 7/135; A61K 7/035
[52] U.S. Cl. .................. 424/78.02; 424/78.03; 424/62; 424/69; 424/70.1; 424/70.17; 424/70.19; 252/8.6; 252/8.8; 252/357

[58] Field of Search ............... 252/8.6, 8.8, 357, 252/DIG. 5; 424/70.17, 62, 69, 70.1, 78.02, 78.03, 70.19

[56] References Cited

U.S. PATENT DOCUMENTS

5,401,426  5/1995  Gerling et al. ................ 252/8.6

OTHER PUBLICATIONS

T. J. Williams et al., Carb. Res. 67:C1–C3, 1978.

*Primary Examiner*—John W. Rollins
*Attorney, Agent, or Firm*—Evenson, McKeown, Edwards & Lenahan

[57] ABSTRACT

Lactobionic acid amide compositions synthesized from lactobionic acid and a mixture of primary fatty amines, which contains at least 30 percent by weight of fatty amines having a chain length of 14 to 18 carbon atoms, and their use as softening, detergent, emulsifying, foam stabilizing and/or thickening components of detergents, rinsing or cleaning agents, softeners or cosmetic formulations.

2 Claims, No Drawings

LACTOBIONIC ACID AMIDE COMPOSITIONS AND THEIR USE

CROSS REFERENCE TO RELATED APPLICATION

This application is a division of my application Ser. No. 08/136,371, filed Oct. 15, 1993, U.S. Pat. No. 5,401,426, which is a continuing application of U.S. patent application Ser. No. 07/974,164, filed May 11, 1992, now abandoned.

BACKGROUND OF THE INVENTION

This invention relates to new lactobionic acid amide compositions comprising amide mixtures obtained from lactobionic acid and fatty amine mixtures, and to the use of such lactobionic acid amide compositions.

German Patent No. DE 1,155,771 discloses the synthesis of N-alkyl amides of maltobionic, lactobionic and cellobionic acids with 6 to 12 carbon atoms in the alkyl group by reacting the respective acid lactone with the alkylamine in dimethylformamide. The patent states that these amides have surface active properties.

SUMMARY OF THE INVENTION

It is the object of the present invention to provide new surface active compositions which are obtainable from renewable raw material sources.

Another object of the invention is to provide a new surface active composition which is biodegradable.

A further object of the invention is to provide a composition which can be used as a component with detergent, foam stabilizing or thickening properties in a liquid washing or rinsing composition or in a cosmetic formulation.

It is also an object of the invention to provide a new surface active composition which is particularly suitable for use in an aqueous system.

These and other objects of the invention are achieved in accordance with the invention by providing a lactobionic acid amide composition comprising amides of lactobionic acid with a mixture of primary fatty amines containing at least 30 percent by weight fatty amines having a chain length of 14 to 18 carbon atoms.

DETAILED DESCRIPTION OF PREFERRED EMBODIMENTS

It has now been discovered that amide mixtures from amides of lactobionic acid formed by reacting lactobionic acid with mixtures of higher fatty amines also have, in addition to from good surface active properties, a good solubility and good foam stabilizing properties in aqueous systems. Furthermore, because of their outstanding application properties, they are suitable as softening, detergent, emulsifying, foam stabilizing and/or thickening components in detergent, rinsing agent and cleaning agent compositions, in softeners, particularly fabric softeners, and in cosmetic formulations.

The invention therefore relates to lactobionic acid amide compositions from amides of lactobionic acid with a mixture of primary fatty amines, which contains at least 30 percent by weight of fatty amines with a chain length of 14 to 18 carbon atoms, and to the use of such lactobionic acid compositions.

As used herein the term "primary fatty amines" refers to primary amines which contain a linear, aliphatic group corresponding to the aliphatic group of a fatty acid. Fatty amines can be obtained industrially, for example, from fatty acids by first converting the fatty acids into the corresponding nitriles, and subsequently reducing the nitriles to the corresponding amines.

The lactobionic acid amide compositions of the invention can be obtained by reacting lactobionic acid or reactive lactobionic acid derivatives, particularly lactobionic acid lactone, with an appropriate fatty amine mixture by known methods. In order to synthesize the lactobionic acid amide compositions of the invention, fatty amine mixtures are used which contain at least 30 percent by weight fatty amines having a chain length of 14 to 18 carbon atoms. Fatty acid mixtures containing at least 90 percent by weight, for example 90 to 98 percent by weight, of fatty amines having a chain length of 16 to 18 carbon atoms, have proven to be particularly advantageous. Preferably, fatty amine mixtures are used, which contain about 5 to 85 percent by weight and, particularly, 35 to 85 percent by weight of mono-unsaturated fatty amines.

Lactobionic acid (= 4-(β-D-galacto)-D-gluconic acid) and lactobionic acid lactone, as well as their synthesis, are already known. Lactobionic acid can be obtained, for example, by oxidation of lactose using a known procedure.

Preferably, fatty amine mixtures obtained from naturally occurring fatty acid mixtures are used. The proportion of mono-unsaturated fatty amines in these fatty amine mixtures varies between about 5 and 85 percent by weight. Examples of suitable fatty amine mixtures include coconut oil fatty amine from the fatty acid mixture originating from coconut oil, tallow amine and hydrogenated tallow amine from the fatty acid mixture originating from tallow, and oleyl amine from the fatty acid mixture originating from sunflower oil and/or soybean oil. Coconut oil fatty amine contains, for example, about 50 percent by weight of saturated $C_{12}$ fatty amines, about 18 percent by weight of saturated $C_{14}$ fatty amines, as well as about 7 percent by weight of unsaturated $C_{18}$ fatty amines. Hydrogenated tallow amine contains, for example, about 30 percent by weight of saturated $C_{16}$ fatty amines, about 60 percent by weight of saturated $C_{18}$ fatty amines as well as about 3 percent by weight of unsaturated fatty amines with 14 to 18 carbon atoms. Tallow amine contains, for example, about 29 percent by weight of saturated $C_{16}$ fatty amines, about 23 percent by weight of saturated $C_{16}$ fatty amines, as well as about 42 percent by weight of unsaturated fatty amines with 14 to 18 carbon atoms. Oleyl amine, obtained from sunflower oil, contains, for example, about 14 percent by weight of saturated fatty amines with 12 to 18 carbon atoms and about 85 percent by weight of unsaturated fatty amines with 14 to 18 carbon atoms. Oleyl amine, obtained from soybean oil (= soybean amine), contains, for example, about 16 percent by weight of saturated $C_{16}$ fatty amines, about 15 percent by weight of saturated $C_{18}$ fatty amines, as well as about 63 percent by weight of unsaturated fatty amines with 14 to 18 carbon atoms.

The invention further relates to a process for producing the lactobionic acid amide compositions according to the invention. The lactobionic acid amide compositions according to the invention are produced by reacting lactobionic acid or a reactive derivative thereof, such as lactobionic acid lactone, with the fatty amine mixture, in a lower alkyl alcohol, preferably in a lower alkyl alcohol with 1 to 4 carbon atoms, such as methanol, isopropanol or ethanol, to obtain a lactobionic acid amide composition according to the invention. The reaction is usually carried out by dissolving or suspending the lactobionic acid or, preferably, the lactobionic acid lactone in the alcohol and adding the fatty amine mixture slowly, dropwise, with stirring. The mixture is thereafter stirred or homogenized for about 1 to 3 hours at 0° to 5° C. The solution or suspension optionally may then be allowed to stand for 1 to 18 hours, so that the reaction product crystallizes out completely. The lactobionic acid amide composition of the invention precipitates as a sediment, which is washed and dried in a drying oven, optionally under vacuum.

It is surprising that the lactobionic acid amide according to the invention can also be produced in a suspension, like that which exists when the reaction is carried out in ethanol or isopropanol, so that the use of the previously proposed dimethylformamide, which is toxicologically objectionable, can be avoided.

It is an advantage of the amide mixtures of the invention that they consist exclusively of components of natural origin, such as lactose (in the lactobionic acid group) and fatty acids (in the long-chain amide group). Furthermore, because of their synthesis in a lower alcohol, they do not contain any residues of toxicologically objectionable substances. Consequently, they are compatible with the skin and are readily biodegradable.

The lactobionic acid amide compositions of the invention can be easily obtained on the basis of a secure raw material base and accordingly are also advantageous from an economic point of view.

The lactobionic acid amide compositions of the invention exhibit surprisingly good properties for technical applications. In aqueous systems, the lactobionic acid amide compositions according to the invention have good surface active properties together with favorable foaming behavior. Thus, the lactobionic acid compositions according to the invention not only exhibit a strong foaming capacity, but they also have a many-fold lower (and consequently more favorable) critical micelle forming concentration in cleaning compositions, compared to the known lactobionic acid-N-dodecyl amide. The compositions of the invention, therefore, can be advantageously used as detergent (cleaning as well as softening), emulsifying, foam-stabilizing and/or thickening, surface active components in detergent and rinsing and cleaning agent compositions and also in softeners and cosmetic formulations. Depending on the intended use, these compositions can, of course, contain other conventional ingredients, so that the concentration of the lactobionic acid amide composition according to the invention in such preparations can vary throughout a wide range, for example between 0.1 and 80 wt-%, based on the total weight of the preparation.

The lactobionic acid amide compositions according to the invention can be used as surface active components with a good detergent effect in washing, cleaning and rinsing compositions. In such compositions the lactobionic acid amide compositions according to the invention advantageously may be used in concentrations in the range from 0.1 to 50 wt-%. In particular, the N-coconut oil amide of lactobionic acid is distinguished by the formation of a stable foam in addition to having a surprisingly high solubility, which is desirable, for example, for use in laundry detergents or dishwashing detergents for washing dishes by hand or in cosmetic formulations, such as bubble baths or hair shampoos.

The amide mixtures of the invention are also very suitable as components of cosmetic formulations, in which they can act as emulsifiers and/or thickeners. The N-oleyl amide and also the N-tallow amide of lactobionic acid are suitable as emulsifying additives, for example in concentrations of from 0.5 to 15 wt-%, in particular from 5 to 15 wt-%, based on the total weight of the emulsion. The N-oleyl amide of lactobionic acid is particularly suitable as a thickener, since, because of its good solubility in water, it can be used in a concentration sufficient for forming a wetting or cross linking structure. When lactobionic acid N-oleyl amide is used as a thickener, its concentration should advantageously lie in the range from 2 to 15 wt-%, based on the weight of the total preparation. Depending on the concentration used, thickened liquids, viscous non-flowing semi-solid gels, or semi-solid gels almost firm enough to be sliced can be produced. An aqueous solution containing, for example, 6 percent by weight of the N-oleyl amide of lactobionic acid has a viscous consistency, while an aqueous solution containing 12 percent by weight of the N-oleyl amide of lactobionic acid has the consistency of a clear gel almost firm enough to be sliced.

Compositions formed with the lactobionic acid amide mixtures of the invention may also contain any of the usual vehicles, diluents and/or adjuvants used as ingredients in conventional detergent, rinsing or cleaning compositions or cosmetic formulations.

Emulsions prepared with the compositions of the invention have consistencies which exhibit very good long-term stability.

Moreover, the lactobionic acid amide compositions according to the invention are also very useful as softening ingredients of softeners, particularly of fabric softeners. The N-oleyl amide or the N-tallow amide of lactobionic acid is particularly suitable for this purpose. A good fabric softening effect is achieved with an aqueous solution containing 0.01 to 15 wt-%, in particular 0.01 to 5 wt-% of a mixture of N-amides of lactobionic acid. Besides the conventional additives in fabric softeners, other softening substances may also be contained. For example, in addition to the lactobionic acid amide composition of the invention, fabric softener formulations according to the invention may also contain customary amounts of other components usually found in fabric softeners, such as scents, dyes, pigments, opacifiers, optical brighteners, corrosion inhibitors, water-soluble polymers or anti-static agents. The lactobionic acid amide compositions according to the invention are advantageously used in a concentration of 1 to 80 percent by weight, based on the total formulation of the fabric softener. It is surprising that the lactobionic acid amide compositions of the invention have such good softening properties, particularly fabric softening properties, although their structure differs greatly from that of previously used softening ingredients of fabric softeners, which generally are cationic, quaternary ammonium compounds. Compared to the cationic ammonium compounds previously used as fabric softeners, which are well known to be difficult to decompose biologically and which therefore contribute to increased pollution of the environment, the lactobionic acid amide compositions of the invention differ advantageously in that they can be readily decomposed by biological means.

The following examples are intended to illustrate the invention in further detail without, however, limiting its scope.

EXAMPLES

1. Synthesis of Lactobionic Acid N-Oleyl Amide:
   a) Synthesis in methanol:

Lactobionic acid lactone (500 g) was finely ground in a mortar and then dissolved in portions in 1.6 liters of methanol at 50° to 60° C. To this solution, 324.4 g of oleylamine were slowly added dropwise with stirring. This solution, which was still clear, was cooled on ice and stirred for a further hour. It was then allowed to stand for about 12 hours. A white sediment precipitated, which was filtered out, washed with methanol, and then dried in a vacuum oven at 40° to 50° C. The yield was 93 percent by weight of the N-oleyl amide of lactobionic acid, based on the lactobionic acid lactone.

b) Synthesis in isopropanol:

Five hundred grams of lactobionic acid lactone were finely ground in a mortar and then suspended in portions in 1000 ml of isopropanol at 50° to 60° C. by means of a homogenizer. A known fine grinding mill (Type PUC-NA) was used as the homogenizer in order to obtain better mixing of the resulting suspension. 326 g of oleyl amine were heated to approximately 40° to 50° C. and added dropwise to the suspension while homogenization was continued. The completed suspension was homogenized for an additional hour while cooling with ice and subsequently allowed to stand for about 12 hours. A white precipitate was filtered out, washed with isopropanol and then dried in a vacuum dryer at 40° to 50° C. The yield of lactobionic acid N-oleyl amide was 90 wt-% based on the lactobionic acid starting material.

Lactobionic acid N-oleyl amide was also synthesized in ethanol as a solvent in a manner analogous to the synthesis in isopropanol described in Example 1. b).

The other lactobionic acid amide compositions according to the invention were also synthesized as described above for lactobionic acid N-oleyl amide by way of example.

2. a) Determination of Foaming Capability:

The foaming capability of the lactobionic acid amide composition of the invention was determined as described in the following, by a modified Rose-Miles method based on DIN 53902, part 2.

To test the foaming capability, 1,000 ml of a 0.1 percent by weight aqueous solution of the lactobionic acid amide mixture according to the invention was prepared.

The apparatus used comprised two glass vessels disposed one above the other, each equipped with a thermostat. About 20 ml of the solution, the temperature of which had previously been adjusted to 50° C., were introduced into the lower vessel, and 500 ml of the solution were added to the upper vessel. The solution was then allowed to run from the upper vessel through a capillary into the solution in the lower vessel. The height of the resulting foam was measured after 30 seconds, 3 minutes and 5 minutes. The following Table 1 shows the results obtained.

TABLE 1

| Lactobionic Acid Amide | Foam Height in mm after | | |
|---|---|---|---|
| Composition | 30 sec. | 3 min. | 5 min. |
| N-coconut oil amide of lactobionic acid | 190 | 190 | 188 |
| N-oleyl amide of lactobionic acid | 90 | 86 | 85 |
| N-tallow amide of lactobionic acid | 65 | 65 | 63 |

The results shown in Table 1 confirm the good foaming capability of the lactobionic acid amide compositions of the present invention. The foam obtained had very fine pores and was still stable even after an extended period of time. A large amount of foam, which remained stable for a long time, was produced particularly with the N-coconut oil amide of lactobionic acid. The N-coconut oil lactobionic acid amide is therefore very useful in cosmetic preparations in which a large and stable amount of foam is desirable, for example, in bubble baths or hair shampoos.

2. b) Surface tension, critical micelle forming concentration:

The surface tension and critical micelle forming concentration (C.M.C.) of the lactobionic acid amide compositions according to the invention were determined in a known manner. For this purpose the force exerted by the surface tension was measured with a tensiometer following DIN 53914 which must be applied in order to withdraw a ring suspended horizontally to the surface of the liquid from the surface of the liquid. Table 1a shows the values which were obtained.

TABLE 1a

| Lactobionic acid amide Composition | Surface Tension [mN/ml; 0.1 g/l] | C.M.C. [g/l] |
|---|---|---|
| N-coconut oil amide of lactobionic acid | 34 | 0.01 |
| N-oleyl amide of lactobionic acid | 31 | 0.01 |
| N-tallow amide of lactobionic acid | 35 | 0.01 |

The values determined for the surface tension and for the C.M.C. confirm the good detergent properties of the lactobionic acid amide compositions according to the invention for use as surface active agents in laundry detergents or cleaning solutions.

3. Use of Lactobionic Acid N-Oleyl Amide as an Emulsifier:

The N-oleyl amide of lactobionic acid, water and thistle oil were homogenized in the concentrations given in Table 2 below in a beaker at 60° to 70° C. with a homogenizer ("Ultraturrax"). In addition, 0.1 percent by weight of formaldehyde was added to the emulsions as preservative. The following Table 2 shows the results obtained. The concentrations are given in terms of percent by weight based on the total weight of the emulsion.

TABLE 2

| N-Oleyl Amide of Lactobionic Acid (% by weight) | Water (% by weight) | Thistle oil (% by weight) | Color and Consistency of the Resulting Emulsion |
|---|---|---|---|
| 5 | 85 | 10 | white emulsion |
| 5 | 75 | 20 | white emulsion |
| 7 | 70 | 23 | white, thickened emulsion |
| 10 | 75 | 15 | white semi-solid gel |
| 10 | 65 | 25 | white semi-solid gel |
| 10 | 50 | 40 | white semi-solid gel |
| 15 | 55 | 30 | white semi-solid gel |

A further experiment was carried out as described above, except that ethoxylated-11-tallow fat was used as the oil phase. The following results were obtained.

| N-Oleyl Amide of Lactobionic Acid (% by weight) | Water (% by weight) | Ethoxylated Tallow Fat (11 EO) (% by weight) | Color and consistency of the Resulting Emulsion |
|---|---|---|---|
| 10 | 87 | 3 | white semi-solid paste |

Even after three weeks of standing, no changes were detected in the color and consistency of the emulsions obtained. Thus, the emulsions prepared with the N-oleyl amide of lactobionic acid exhibited very good long-term stability.

4. Use of Lactobionic Acid N-Oleyl Amide as a Thickener:

Aqueous solutions were prepared containing from 2 to 12% N-oleyl amide of lactobionic acid and homogenized with a homogenizer at 60° to 70° C. Table 3 shows the results obtained when the N-oleyl amide of lactobionic acid was used as a thickener.

TABLE 3

| N-Oleyl Amide of Lactobionic Acid | Water (% by weight) | Color and consistency of the Resulting Product |
| --- | --- | --- |
| 2 | 98 | Colorless, clear liquid |
| 4 | 96 | White thickened clear liquid |
| 6 | 94 | White viscous clear liquid |
| 8 | 92 | White non-flowing clear gel |
| 10 | 90 | White semi-solid clear gel |
| 12 | 88 | White semi-solid clear gel almost firm enough to be sliced |

The results obtained show the good thickening action of the N-oleyl amide of lactobionic acid. Depending on the concentration of N-oleyl amide of lactobionic acid which is used, different degrees of thickening can be obtained. The clarity of the formulations, which is possible because of the good solubility of the N-oleyl amide of lactobionic acid, is especially advantageous. The N-oleyl amide of lactobionic acid is therefore ideally suited for use as a thickener, for example in cosmetic creams, ointments, pastes or gels.

5. Use of Lactobionic Acid N-Oleyl Amide or N-Tallow Amide in Fabric Softeners:

Softener experiments were also carried out with lactobionic acid amide compositions. For these experiments, 10×10 cm cloths were cut from a cotton terry cloth and immersed completely with stirring in an aqueous solution containing 0.15 g/600 ml of a lactobionic acid amide composition according to the invention, which is to be tested. The cloths were subsequently wrung out by hand and dried in air. As a comparison, a cloth was treated in an analogous manner only with water. The dried cloths were tested by 10 persons for softness and given a grade from 1 to 4. The comparison cloth, which had been treated only with water, was assigned a softness value of zero. Table 4 shows the average values assigned in the evaluation of the softness.

TABLE 4

| Softener Rinse Solution Consisting of Water Containing as a Softener | Softness Achieved with the Treated Cloth |
| --- | --- |
| — | 0 |
| N-oleyl amide of lactobionic acid | 3.0 |
| N-tallow amide of lactobionic acid | 3.7 |

Experiments were also carried out in an analogous manner with solutions which contained lactobionic acid n-oleyl amide or lactobionic acid N-tallow amide in a concentration of 0.6 g per 600 ml and 1.2 g per 600 ml. These test values also corresponded to the results given in Table 4. The results show that the lactobionic acid amide compositions have a good fabric softening effect.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A cosmetic formulation comprising:
   a) an effective detergent, emulsifying, foam-stabilizing or thickening amount in the range from 1 to 80 percent by weight, based on the total weight of said formulation, of a surface active lactobionic acid amide composition comprising lactobionic amides produced from the reaction of lactobionic acid and a mixture of primary fatty amines obtained from a naturally occurring fatty acid mixture and containing at least 30 percent by weight fatty amines having a chain length of 14 to 18 carbon atoms, and
   b) from 20 to 99 percent by weight of at least one conventional vehicle or adjuvant ingredient for cosmetic formulations.

2. A composition according to claim 1, wherein said composition is a cosmetic gel formulation containing a thickener, and said lactobionic acid amide composition is used as said thickener.

* * * * *